United States Patent
Rajadhyaksha et al.

[11] 3,984,501
[45] Oct. 5, 1976

[54] PHENYL- AND BENZYLPHOSPHONATE ESTERS

[75] Inventors: Vithal J. Rajadhyaksha, Mission Viejo; James V. Peck, Newport Beach; Julia J. Chouw, Orange, all of Calif.

[73] Assignee: Nelson Research & Development Company, Santa Ana, Calif.

[22] Filed: Feb. 3, 1975

[21] Appl. No.: 546,216

[52] U.S. Cl. .............................. 260/946; 260/329 P; 260/330.5; 260/346.1 R; 260/347.3; 260/347.4; 260/347.7; 260/347.8; 260/940; 260/941; 260/942; 260/943; 260/944; 260/945; 260/951; 260/953; 260/954; 260/955; 260/956; 260/961; 424/210; 424/211; 424/212; 424/214; 424/217; 424/218; 424/219; 424/222

[51] Int. Cl.² .......................................... C07F 9/40

[58] Field of Search .......... 260/940, 941, 942, 943, 260/944, 945, 946, 951, 953, 954, 955, 956, 961

[56] References Cited
UNITED STATES PATENTS

| | | | |
|---|---|---|---|
| 2,329,707 | 9/1943 | Farrington et al. | 260/958 X |
| 3,019,249 | 1/1962 | Gunderloy | 260/961 X |
| 3,268,629 | 8/1966 | Cherbuliez et al. | 260/961 X |
| 3,851,019 | 11/1974 | Hogberg et al. | 260/946 |
| 3,862,270 | 1/1975 | Hogberg et al. | 260/946 |
| 3,869,527 | 3/1975 | Hogberg et al. | 260/946 |

*Primary Examiner*—Richard L. Raymond
*Attorney, Agent, or Firm*—Martin A. Voet

[57] ABSTRACT

Compounds having the structural formula

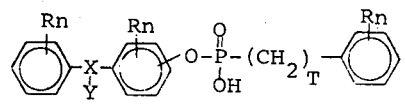

wherein X is an alkyl or alkenyl chain having 2–8 carbon atoms, one of which carbon atoms may be in the form of a carbonyl group, Y is H, alkyl, dialkylaminoethyl, aryl, aralkyl or aryl and aralkyl substituted with one or more R, and R is H, lower alkyl, lower alkoxy, halogen, $CF_3$, $NO_2$, OH, CN, $COOR_1$,

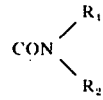

$NHCOR_1$, $NR_1R_2$ or

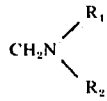

where $R_1$ and $R_2$ are each selected from the group consisting of H and lower alkyl; R, $R_1$ and $R_2$ being the same or different, T is 0 or 1 and $n$ is 0–5; and pharmaceutically acceptable salts thereof.

7 Claims, No Drawings

PHENYL- AND BENZYLPHOSPHONATE ESTERS

BACKGROUND OF THE INVENTION

1. Field of the Invention

The present invention generally relates to novel compounds. More particularly, the present invention relates to novel compounds having prostaglandin-blocking activity.

2. Background of the Prior Art

French patent publication Nos. 2,150,791 and 2,150,792 disclose phenyl phosphate esters related to the phenyl- and benzyl-phosphonate esters set forth in the present application as being selective inhibitors of prostaglandin and slow reacting substance, a substance related to prostaglandin, having smooth muscle stimulatory activity.

SUMMARY OF THE INVENTION

We have now discovered a class of phenyl- and benzyl-phosphonate esters which are substantially more active and/or less toxic prostaglandin-blocking compounds than the phenyl phosphate esters heretofore known.

This invention is concerned with compounds having the structural formula

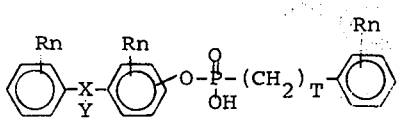

wherein X is an alkyl or alkenyl chain having 2-8 carbon atoms, one of which carbon atoms may be in the form of a carbonyl group, Y is H, alkyl, dialkylaminomethyl, aryl, aralkyl or aryl and aralkyl substituted with one or more R, and R is H, lower alkyl, lower alkoxy, halogen, $CF_3$, $NO_2$, OH, CN, $COOR_1$,

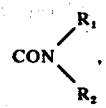

$NHCOR_1$ $NR_1R_2$ or $CH_2NR_1R_2$ where $R_1$ and $R_2$ are each selected from the group consisting of H and lower alkyl; R, $R_1$ and $R_2$ being the same or different, and $n$ is 0–5; T is 0 or 1 and pharmaceutically acceptable salts thereof.

The method of the present invention utilizes an active compound together with a pharmaceutical carrier therefor and relates to methods for treating inflammation or diarrhea or other conditions which are prostaglandin-mediated in animals including humans comprising administering to an animal a composition containing an effective amount of one of the active compounds described above together with a suitable pharmaceutical carrier.

DETAILED DESCRIPTION OF THE INVENTION

The active compounds of the present invention have the structural formula

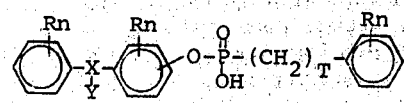

Referring more particularly to the active compounds, X is an alkyl or alkenyl chain having 2–8 carbon atoms and preferably 3–5 carbon atoms, one of which carbon atoms may be in the form of a carbonyl group.

Y may be hydrogen or straight or branch chain alkyl radicals having 1–12 carbon atoms, such as, for example, methyl, ethyl, propyl, iso-propyl, n-butyl, pentyl, hexyl, heptyl, etc.; aryl, such as, for example, phenyl, 1- and 2-napthyl, biphenylyl, 2- or 3-thienyl, 2- or 3-benzo[b]thienyl, 2- or 3-furyl, 2- or 3-indenyl, etc.; and aralkyl, such as, for example, benzyl, phenethyl, 1- and 2-naphthylmethyl, biphenylmethyl, 2- or 3-thienylmethyl, etc. Y may also be aryl or aralkyl substituted with one or more substituents R and dialkylaminomethyl such as dimethylaminomethyl.

The substituent R is H, lower alkyl or lower alkoxy, that is, having 1–3 carbon atoms and preferably 1–2 carbon atoms, halogen and preferably —Br, —Cl or —F, $CF_3$, $NO_2$, OH, CN, $COOR_1$, $CONR_1R_2$, $NHCOR_1$, $NR_1R_2$ or —$CH_2NR_1R_2$ where $R_1$ and $R_2$ are H or lower alkyl, that is, having 1–3 carbon atoms and preferably 1–2 carbon atoms and $n$ is 0–5 R substituents. Further, R, $R_1$ and $R_2$ may be the same or different. Preferred R substituents are Br and Cl.

T is either 0 or 1, that is, in one ester series the phosphorous atom is linked directly to the benzene ring (T=0) and in the other it is linked to the benzene ring through a methylene group (T=1).

Preferred active compounds include those compounds of the foregoing structural formula wherein X is an alkyl or alkenyl chain having 3 carbon atoms, with or without a carbonyl group, R is H and Y is a benzyl group or benzyl group substituted with Br or Cl, preferably in the para position.

The compound may have the phosphorous atom linked through a phenolic oxygen in positions 2, 3 or 4 but preferably in the 4 position of the benzene ring. The compound in question may also be in the form of a pharmaceutically acceptable salt.

The phenyl- and benzylphosphonate esters of the invention may be prepared by treating an appropriately substituted phenol of the formula

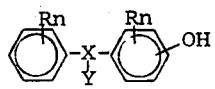

with a phosphorylating agent. The preferred phosphorylating agents are phenyl- and benzylphosphonic dichloride. However, this does not restrict the use of $P,P_1$-diphenyl- and $P,P_1$-dibenzyl-pyrophosphonate or phenyl- and benzylphosphonic acid and a condensing agent. Condensing agents for this use are carbonyldiimidazole, dicyclohexylcarbodiimide and others mentioned in "Phosphonsaure und Derivate", K. Sasse in Houben-Weyl, Methoden der Organischen Chemie, Vol. 12, part I.

A tertiary base may be used in the phosphorylation reaction especially if hydrogen halide is evolved during the reaction. Preferred bases are pyridine and diisopropylethylamine.

The above-described appropriately substituted phenols are conveniently synthesized by condensing an appropriately substituted acetophenone with an appropriately substituted benzaldehyde. This Claissen- Schmidt condensation is conveniently carried out in the presence of an acid or base catalyst depending upon the nature of the substituents on the benzene ring. Where X is 3 carbon atoms, the methoxy substituent on the acetophenone or benzaldehyde determines its position with the carbonyl group. This is outlined below as follows:

diphenylethanone with an appropriately substituted benzaldehyde in presence of piperidine. The product is then cleaved in refluxing glacial acetic acid to obtain an aryl substituted derivative of 1,3-diphenyl-2-propen-1-one substituted at 2 position in the carbon chain. This is then reduced catalytically (Pd/H$_2$) or chemically (Zn/acetic acid) to obtain the 1,3-diphenyl-1-propa-

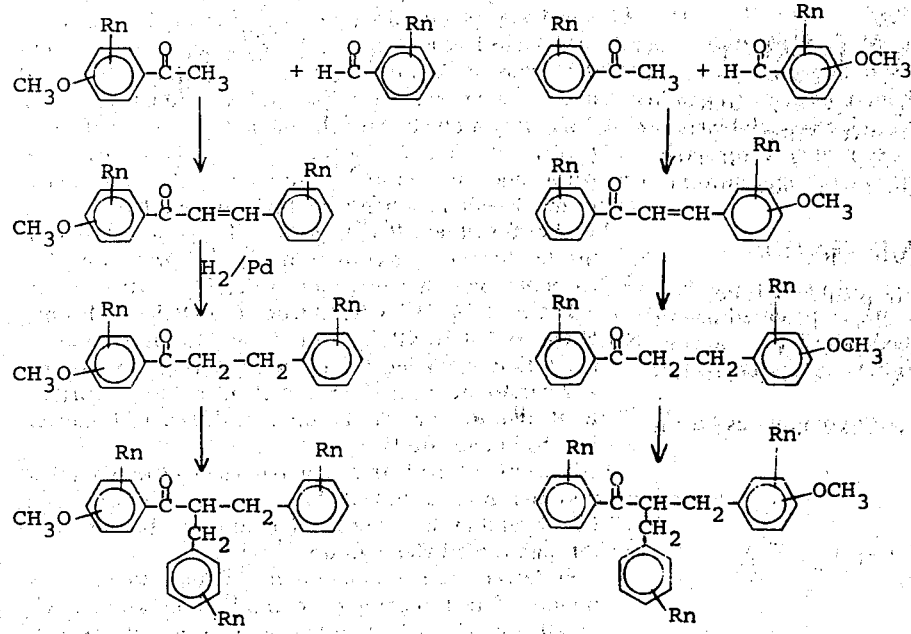

The above outline shows a 1,3-diphenyl-2-propen-1-one derivative reduced catalytically with Pd-H$_2$ to the corresponding 1,3-diphenyl-1-propanone derivative which is then alkylated with an appropriately substituted aralkyl halide to give the final compound shown. Potassium-t-butoxide and DMSO may be used as base and solvent respectively.

The final compound is demethylated with pyridine hydrochloride at 200°C to give the desired phenol derivative. Anhydrous aluminium chloride or Boron tribromide may also be used as demethylating agents.

Yet another method for preparation of the phenols is by treating a nuclear hydroxy substituted 1,2- none derivative. This is outlined in the following scheme:

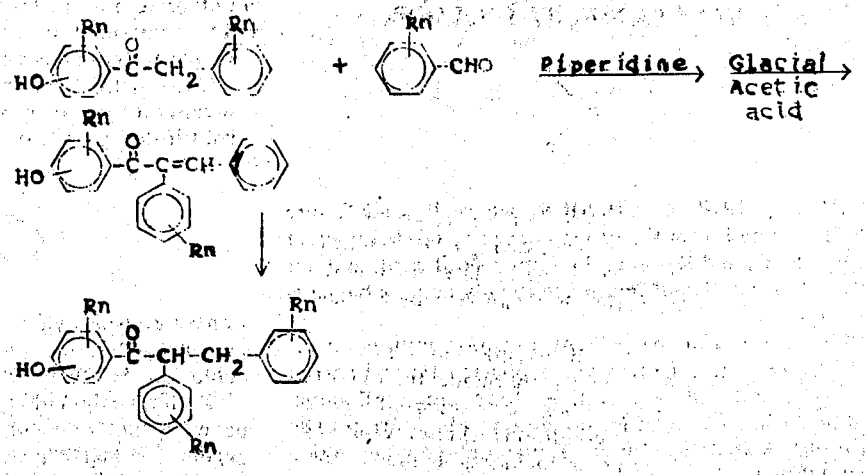

1-(hydroxyphenyl)-1-aralkanones (Y = H) can be prepared by various methods. One method comprises the Friedel-Crafts reaction of an appropriate nuclear substituted or nuclear unsubstituted phenyl ether, such as methoxy- or ethoxybenzene, together with phenylalkanoyl halide in the presence of a metallic halide; followed by hydrolysis of the 1-(alkoxyphenyl)-1-aralkanone intermediate thus producing the desired 1-(-hydroxyphenyl)-1-aralkanone. Suitable metallic halides may be used to prepare either the 2 or the 4 substituted phenol reactant. It frequently occurs that the Friedel-Crafts reaction produces a mixture of the 2- and 4-isomers of the phenol ether reactant; this is particularly so when the phenol ether employed as the starting material contains a substituent in the 3-position of the benzene nucleus, e.g. 3-methoxy chlorobenzene, 3-methoxy toluene, etc. When such a mixture is obtained, it is not necessary to separate the isomeric alkoxy phenyl aralkanones; instead, the mixture may be hydrolyzed to produce the corresponding hydroxyphenyl aralkanones and the isomeric compounds thus produced are then readily separated by distillation.

It is essential that during the alkylation, the phenolic OH group is blocked as an ether. In such cases, where the 2- and 4-alkoxy isomers are obtained, these are converted to phenols, separated and reblocked as alkyl ethers, followed by alkylation and deblocking, giving insertion of a Y substituent. Friedel-Crafts acylation of a nuclear unsubstituted methoxybenzene gives preferentially 4-substituted phenyl ethers.

Still another method for preparing the 1,3-diphenyl-1-propanone derivatives comprises the reaction of a Grignard reagent, either

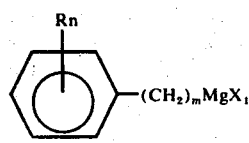

where $X_1$ is a halogen atom, e.g. chlorine, bromine, etc., and m = 1–7; or

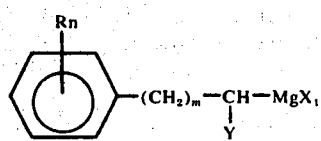

where $X_1$ is a halogen atom, e.g. chlorine, bromine, etc. and m = 1–6,

A substituent Y in the carbon chain of the alkoxyphenyl aralkanone is formed, as mentioned earlier, with potassium t-butoxide in DMSO, followed by hydrolysis of the alkyl ether. This is outlined in general below.

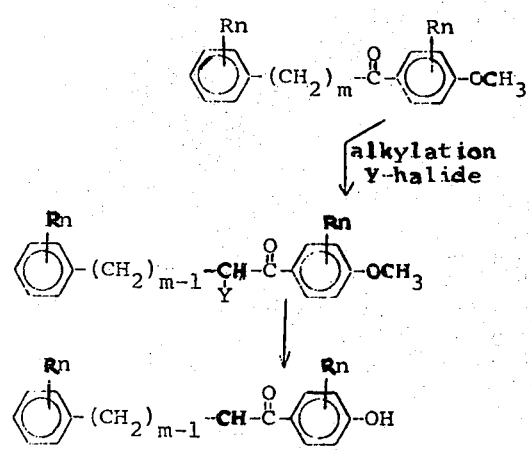

wherein, m = 1 to 7 with an appropriate formula substituted phenol ether of the formula:

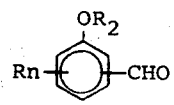

wherein $R_2$ is a lower alkyl, such as methyl, ethyl, etc. and $R_n$ has the same meaning as above.

The alkoxy substituted benzyl alcohol intermediate thus produced is then oxidized to the corresponding ketone derivative. The ether group can be cleaved, if necessary, by conventional methods to obtain the phenol. Oxidizing agents suitable for use in the process include, for example, sodium dichromate dihydrate, etc. The alkoxy compound is then alkylated, followed by hydrolysis of the ether to the phenol. This route may be employed to prepare all 2, 3 and 4-alkoxy or hydroxy substituted compounds, and is very convenient for 3-alkoxy or hydroxy derivatives. For example, a 3-formyl methoxybenzene will react with the appropriate Grignard reagent to produce the corresponding 3-methoxy substituted benzyl alcohol and the said alcohol is then oxidized to the ketone derivative.

The carbonyl group in all the phenols is chemically reduced either with Zn/acetic acid (Clemmenson Reduction) or with hydrazine hydrate and KOH (Wolff-Kischner Reduction) to obtain the completely saturated derivatives of the present invention, which are phosphorylated in the manner described earlier.

The saturated diphenylalkane derivatives are also prepared by addition of a Grignard reagent

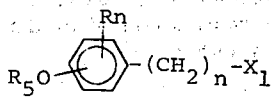

to a compound of formula

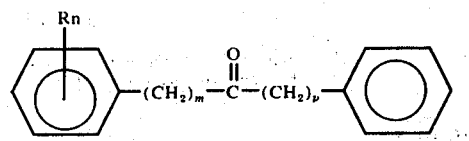

wherein $X_1$ is halogen such as chlorine or bromine, P is 1–5, $R_5$ is a lower alkoxy group, $m$ is 1–7, $n$ is 1–7, but $(m + n)$ not exceeding 7.

For example, if $m$ is 4, then $n$ can be 1–3.

The so-obtained tertiary alcohol is dehydrated and then catalytically reduced to the saturated compound, which is demethylated (hydrolysis of alkoxy group) and phosphorylated in the manner described above.

The Y substituent dialkylaminoalkyl may be introduced by a Mannich reaction of a carbonyl compound

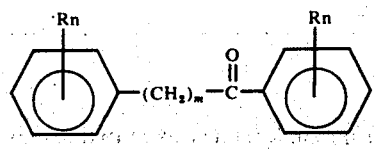

with paraformaldehyde and a secondary amine

wherein $R_6$ and $R_7$ are lower alkyl groups and preferably methyl.

Yet another method for synthesis of appropriately substituted phenols is to react a bromo substituted phenol ether with an araliphatic aldehyde in presence of magnesium metal in ether as shown below:

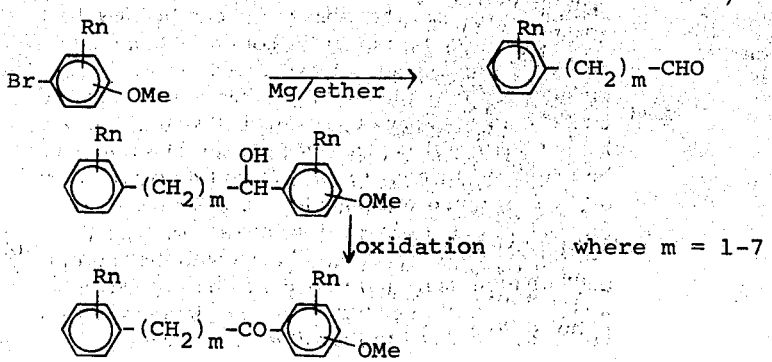

The resulting compound may be alkylated as described earlier, demethylated and phosphorylated.

The term "pharmaceutically acceptable salt" as used herein and in the appended claims refers to those pharmaceutically acceptable salts conventionally employed, such as sodium, potassium, ammonium, and triethylammonium salts.

The term "animals" as used herein and in the appended claims refers generally to mammals and includes domesticated animals and humans.

Pharmaceutical compositions may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

Aqueous suspensions contain the active ingredients in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

Topical carriers include conventional topical carriers such as ointments, aqueous solutions, aerosols, suspensions or oil suspensions.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 10 mg and about 500 mg of the active ingredient of the formula stated above.

From the foregoing formulation discussion, it is apparent that the compositions of this invention can be administered topically, orally or parenterally. The term parenteral as used herein includes subcutaneous injection, intravenous, intramuscular, or intrasternal injection or infusion techniques.

This invention is further demonstrated by the following examples in which all parts are by weight.

EXAMPLE I

Method of making benzylphosphonate monosodium salt of 1-(4-hydroxyphenyl)-2-(4-chlorobenzyl)-3-phenyl-1-propanone having the structural formula

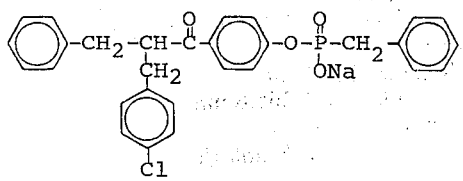

50.1 g. (0.333 m) 4-methoxyacetophenone and 35.4 g (0.333 m) benzaldehyde were combined in a 500 ml Erlenmeyer flask, with the 4-methoxyacetophenone being previously melted. Then 80 ml 5N NaOH solution (appr.) (1.2 × 0.333 m) was added to the mixture. Approximately 40 ml absolute ethanol was added to the stirred mixture in small portions to keep the mixture homogeneous. It was let stir at room temperature overnight, and a solid white cake resulted. The solid was filtered, washed with water, and then recrystallized from methanol/water to give 72.3 g (91%) of 1-(4-methoxyphenyl)-3-phenyl-2-propen-1-one. 10 g (0.0420 m) of this compound and 160 mg Pd on C (10%) were combined with about 200 ml ethyl acetate and placed under 1 atm of hydrogen. Upon stirring, the mixture absorbed 950 ml $H_2$ (calc. 940 ml) and stopped. The reaction mixture was filtered and the clear solution was concentrated to obtain 9.8 g (98%) of 1-(4-methoxyphenyl)-3-phenyl-1-propanone.

A solution of 4.23 g (0.01760 moles) of this compound in 20 ml DMSO was added all at once in the presence of nitrogen to 2.11 g (0.0188 moles) potassium t-butoxide in a 100 ml three-neck flask. The mixture was stirred until the solid dissolved. A solution of 3.02 g (0.0188 moles) α,4-dichlorotoluene in 57 ml DMSO was added dropwise through an addition funnel to the reaction flask under nitrogen. The solution was stirred overnight and then 500 ml water and 300 ml chloroform was added. The chloroform layer was separated, and the aqueous layer was extracted with 2 × 100 ml chloroform. The chloroform layer and chloroform extracts were combined, washed with 2 × 200 ml water, dried over anhydrous $MgSO_4$ and concentrated. The residue was dried under vacuum and treated with 6 g of pyridine hydrochloride (0.052 moles) at 210°C for 6 hours. The mixture was cooled and 400 ml of chloroform and 400 ml of water was added. The chloroform layer was separated and the aqueous layer was extracted with 2 × 100 ml chloroform. The chloroform layer and chloroform extracts were combined, washed with 2 × 200 ml water, dried over anhydrous $MgSO_4$ and concentrated. The residue was distilled at 225°–235°C/0.20–0.25 mmHg.

A solution of 1.5 g (0.004275 mole) of the resulting 1-(4-hydroxyphenyl)-2-(4-chlorobenzyl)-3-phenyl-1-propanone in 20 ml pyridine was added to 5.36 g benzylphosphonic dichloride (0.02565 mole) at −10°C and then stirred at room temperature overnight. Unreacted benzylphosphonic dichloride was destroyed by adding water dropwise to the mixture while the reaction flask was immersed in dry ice/acetone bath. Pyridine and water were removed as much as possible on rotatory evaporator at 50°C. 200 ml chloroform and 200 ml 5M HCl were added to the residue and suspended; solid material was filtered off. Chloroform layer was separated and washed with 1N HCl, water and dried over anhydrous $MgSO_4$. Chloroform was removed at reduced pressure. The residue was dissolved in methanol and the pH value was adjusted to 7 with 1N NaOH/methanol. Methanol was removed. The residue was dissolved in water and freeze-dried. Yield: 1.7 g (75.8%).

Ultraviolet

λmax (water) 269 nm
$\epsilon = 11,901.4$
$c = 5.68 \times 10^{-5}$ moles/liter

Chromatography

TLC: one major spot on silica gel in chloroform.

Infrared (Nujol) λmax cm$^{-1}$
2930, 1665, 1595, 1495, 1455, 1410, 1380, 1235, 1190, 1170, 1130, 1070, 1015, 900, 860, 810, 790, 700

Nuclear Magnetic Resonance (CDCl$_3$ TMS)
2.7–3.5δ Multiplet
3.7–4.1 δ Multiplet
7.9–7.7 δ Multiplet
11.5 Singlet

EXAMPLE II

Method of making phenylphosphonate monosodium salt of 1-(4-hydroxyphenyl)-2-(4-chlorobenzyl)-3-phenyl-1-propanone having the structural formula

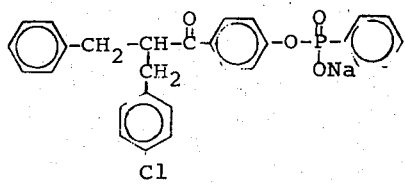

A solution of 2 g (0.0057 mole) of 1-(4-hydroxyphenyl)-2-(4-chlorobenzyl)-3-phenyl-1-propanone in 20 ml pyridine was added dropwise to 6.67 g (0.0342 mole) of phenylphosphonic dichloride at −10°C. The mixture was stirred at room temperature overnight and worked up as under Example I. An oil was obtained which was dissolved in methanol and brought to pH 7 with 1N NaOH/MeOH. Methanol solution was concentrated to 3 ml and 500 ml of ether was added to precipitate the product out. Ether was decanted and the solid was dried. Yield 2.1 g (71.9%).

Chromatography
  TLC— One single spot on silica gel in chloroform.

Ultraviolet
  λ max (water) 266 nm
  ε = 14,623.2
  c = 4.88 × 10$^{-5}$ moles/l Infrared (Nujol) λmax cm$^{-1}$
  2930, 2860, 1678, 1600, 1505, 1495, 1465, 1440, 1415, 1410, 1378, 1368, 1300, 1232, 1225, 1170, 1145, 1075, 1030, 1018, 955, 910, 890, 860, 840, 800, 765, 750, 725, 700, 660, 635

Nuclear Magnetic Resonance (CDCl$_3$ TMS)
  Multiplet 2.5–3.2 δ
  Multiplet 3.3–4.1 δ
  Multiplet 6.8–8.1 δ
  Singlet 11.5 δ

EXAMPLE III

Method of making phenylphosphonate monosodium salt of 1-(4-hydroxyphenyl)-2-(4-bromobenzyl)-3-phenyl-1-propanone having the structural formula

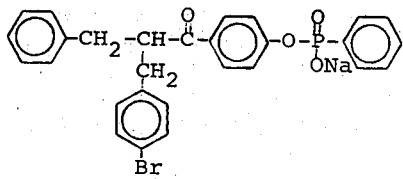

A solution of 4 g (0.01665 moles) 1-(4-methoxyphenyl)-3-phenyl-1-propanone in 50 ml DMSO was added all at once to 1.96 g potassium t-butoxide (0.01748 moles) in a three-neck flask in the presence of nitrogen. The mixture was stirred until it was homogeneous. A solution of 4.35 g α,4-dibromotoluene (0.01748 moles) in 10 ml DMSO was added dropwise through an addition funnel to the reaction flask under nitrogen. The mixture was left at room temperature over the weekend. To the mixture was added 300 ml chloroform and 200 ml water. Organic layer was separated, aqueous layer was extracted three times with 100 ml chloroform. Organic layer and chloroform extracts were combined, washed twice with 200 ml water and dried over anhydrous MgSO$_4$. Chloroform was removed on rotatory evaporator. 4.4 g light yellow oil was obtained. Yield 64.7%. The product contains 8% 1-(4-methoxyphenyl)-3-phenyl-1-propanone as evidenced by gas chromatography analysis on SE 30 column.

A mixture of 4.4 g (0.01075 moles) 1-(4-methoxyphenyl)-2-(4-bromobenzyl)-3-phenyl-1-propanone and 6 g (0.052 moles) pyridine hydrochloride was heated to 200°C for 6 hours. The mixture was cooled and to it was added 200 ml chloroform and 300 ml H$_2$O. Organic layer was separated and aqueous layer was extracted twice with 100 ml chloroform. Organic layer and chloroform extracts were combined, washed with 3 × 105 ml water and dried over anhydrous MgSO$_4$. Chloroform was removed at reduced pressure and the residue was distilled at 238°C/0.2 mmHg. The product is orange, glass-looking solid.

A solution of 2.8 g (0.0071 mole) of 1-(4-hydroxyphenyl)-2-(4-bromobenzyl)-3-phenyl-1-propanone in 30 ml of pyridine was added dropwise to 8.29 g (0.0426 mole) of phenylphosphonic dichloride at −10°C. The mixture was then left overnight and worked up an under Example I. Chloroform solution was concentrated and the residue was dissolved in 100 ml of methanol and pH was adjusted to 7 with 1N NaOH/methanol. Methanol solution was concentrated to 5 ml and ether was added to precipitate the product out. Ether was decanted and the solid was dried. Yield 2.1 g (53.2%).

Chromatography
  TLC: one spot on silica gel in chloroform.

Ultraviolet
  λmax (water) 265.6 nm
  ε = 15,009.8
  c = 5.08 × 10$^{-5}$ moles/l Infrared (Nujol) λmax cm⁻¹
3920, 2860, 1675, 1600, 1505, 1490, 1450, 1380, 1235, 1170, 1145, 1070, 1010, 950, 900, 770, 750, 720, 700

Nuclear Magnetic Resonance (CDCl$_3$ TMS)
  Multiplet 2.4–3.2 δ
  Multiplet 4.1–4.5 δ
  Multiplet 6.8–7.9 δ
  Singlet 13.15 δ

EXAMPLE IV

Method of making benzylphosphonate monosodium salt of 1-(4-hydroxyphenyl)-2-(4-chlorobenzyl)-5-phenyl-1-pentanone having the structural formula $$\text{Ph-CH}_2\text{-CH}_2\text{-CH}_2\text{-CH(CH}_2\text{-C}_6\text{H}_4\text{Cl)-C(=O)-C}_6\text{H}_4\text{-O-P(=O)(ONa)-CH}_2\text{-Ph}$$

A mixture of 13.6 g (0.071 mole) of 5-phenyl-5-oxopentanoic acid, 10 ml (0.175 mole) of hydrazine hydrate (85%), 10.5 g (0.263 mole) of sodium hydroxide and 100 ml of 2,2′-oxydiethanol was heated to 180° to remove water and excess hydrazine. The temperature was raised to 210° and maintained there for 4 hours. The reaction mixture was cooled, chloroform was added, the mixture mixed with 5N hydrochloric acid. The organic layer was separated and washed with (1) 3×150 ml of 5N HCl solution, (2) 3×150 ml of water. The organic layer was then removed, dried (Na$_2$SO$_4$), and solvent removed to yield a solid. This crude product was recrystalized from warm hexane to yield 9.1 g (72%) of product with m.p. 55°–57°.

A mixture of 9.1 g (0.051 mole) of 5-phenylpentanoic acid and 5 ml (0.069 mole) of thionyl chloride was heated until the mixture became homogeneous. Heating was continued for 1 hour; then excess thionyl chloride was distilled under vacuum. Finally, the product was distilled, b.p. 158° at 20 mm to yield 9.6 g (96%) of the acid chloride.

A mixture of 9.6 g (0.049 mole) of 5-phenylpentanoyl chloride, 28 ml (0.257 mole) of methoxybenzene, and 100 ml of dry dichloromethane was cooled to 0°. Anhydrous aluminum chloride, 8.5 g (0.063 mole) was added slowly portionwise with stirring maintaining anhydrous conditions. The reaction mixture was then stirred at room temperature overnight. Circa 70 ml of 5N HCl solution was then added slowly.

The organic phase was separated, washed with 100 ml 1N HCl, 2×100 ml water, and was dried (Na$_2$SO$_4$). Solvent was evaporated and excess anisole was distilled off under reduced pressure. The resultant crystalline residue was recrystalized from warm methanol to yield 10.8 g (82%) of 1-(4-methoxyphenyl)-5-phenyl-1-pentanone.

Under a nitrogen atmosphere, a solution of 8 g (0.03M) 1-(4-methoxyphenyl)-5-phenyl-1-pentanone in 60 ml DMSO was added all at once to 3.7 g (0.033M) potassium t-butoxide. The solution was stirred until all the base had dissolved and then a solution of 5.31 g (0.033M) α,4-dichlorotoluene in 20 ml DMSO was added dropwise. This was let stir overnight. Analysis by gas chromatography of the products through an aliquot workup showed approximately 10% starting material remaining. Thus, portions of base and α,4-dichlorotoluene were added until less than 5% starting material was present. (This amounted to 900 mg (0.00802M) potassium t-butoxide and 1 g (0.00621M) α,4-dichlorotoluene. The mixture was then diluted with 600 ml water and the mixture extracted with chloroform. The organic phase was washed twice with water, dried and concentrated to about 17 g of yellow oil. To this oil was added 14 g (0.121M) pyridine hydrochloride and mixture heated to 200°–205° with stirring under a condenser for 4 hours. After cooling the mass solidified. The residue was shaken with 1N HCl and chloroform, whereupon a brown powder had come out of solution. This was filtered away and washed with chloroform. The organic phase was separated from the filtrate and concentrated to about one-half volume, whereupon more solid had come out of solution. This was filtered and the filtrate run through this procedure until only a small amount of oily residue remained. Cooling and drying the solid gave a yield of 7.9 g (69%).

1.64 g (0.00433M) 1-(4-hydroxyphenyl)-2-(4-chlorobenzyl)-5-phenyl-1-pentanone was dissolved in 30 ml pyridine and added to 5.5 g (0.0263M) benzylphosphonic dichloride. This mixture was kept at −10° to −20° while the addition was continued (1 hour) and 2 hours thereafter. The mixture was then let warm to room temperature and let stir overnight. While cooling the stirred mixture, 5 ml water was slowly added. After stirring 10 minutes, most of the pyridine was removed under reduced pressure and the residue taken up in chloroform. This was washed with 1N HCl, and then 5N HCl. A large amount of benzylphosphonic acid precipitated out. This was filtered away and the organic phase separated. After washing with 3×100 ml portions of 5N HCl and 1×100 ml water, the organic solution was dried and concentration to a light brown oil. This was taken up in methanol and brought to pH 6.9 with methanolic NaOH. Concentration gave a foam which was dissolved in water and freeze-dried to give 2.1 g (91%) of a faint tan powder.

Chromatography
  TLC: (silica gel G, ethyl acetate) one major spot

Ultraviolet — sodium salt
  λmax = 266 nm
  ε = 14,000
  c = 5.4 × 10⁻⁵ moles/liter (water)

Infrared (neat, cm⁻¹) free acid
  3065, 3036, 2940, 2862, 1680, 1600, 1495, 1455, 1410, 1373, 1220, 1165, 1091, 1069, 1015, 990, 928, 835, 809, 793, 752, 698, 660, 642, 588

Nuclear Magnetic Resonance, free acid (CDCl$_3$)
  Broad peak at 11.5 δ
  Multiplet from 6.9–8.2 δ
  Broad multiplet from 2.4–4.0 δ
  Broad peak from 1.4–2.0 δ

EXAMPLE V

Method of making phenylphosphonate monosodium salt of 1-(4-hydroxyphenyl)-2-(4-chlorobenzyl)-5-phenyl-1-pentanone having the structural formula

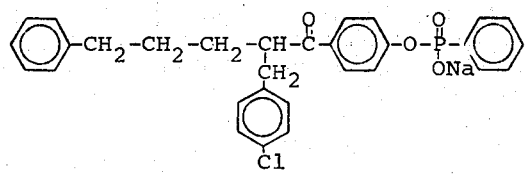

1.64 g (0.00433 M) 1-(4-hydroxyphenyl)-2-(4-chlorobenzyl)-5-phenyl-1-pentanone was dissolved in 30 ml pyridine and added dropwise to a stirred −10° to −20°C mixture of 5.1 (0.0262 M) phenylphosphonic dichloride and 2 ml pyridine. The addition was continued for one hour and the temperature maintained at −6° to −20°C for 2 hours thereafter. This was let warm to room temperature while stirring overnight. Then the mixture was cooled as 5 ml water was slowly added. After stirring 10 minutes, most of the pyridine was removed under reduced pressure. The residue was taken up in chloroform and this washed with 1N HCl (1×75 ml), 5N HCl (3.75 ml), and water (1.75 ml). The organic solution was separated, dried and concentrated to a light brown oil. This was dissolved in methanol and brought to pH 6.9 with methanolic NaOH. Concentration gave a foam which was washed with ether. After decanting the ether and drying, this yielded 1.75 g (76%) of a white powder.

Chromatography
TLC: (silica gel G, ethyl acetate) one major spot

Ultraviolet
$\lambda max = 264$ nm
$\epsilon = 16,400$
$c = 5.84 \times 10^{-5}$ moles/liter (water)

Infrared (neat cm$^{-1}$)
3065, 3033, 2940, 2861, 1680, 1598, 1501, 1493, 1452, 1440, 1410, 1372, 1298, 1220, 1168, 1137, 1092, 1071, 1030, 979, 921, 850, 809, 778, 750, 722, 692, 633, 602

Nuclear Magnetic Resonance (CDCl$_3$)
Broad peak at 12.1 $\delta$
Multiplet from 7.0–8.3 $\delta$
Broad multiplet from 2.35–4.0 $\delta$
Broad peak from 1.3–2.0 $\delta$

EXAMPLE VI

Method of making benzylphosphonate sodium salt of 1-(4-hydroxyphenyl)-2-(4-chlorobenzyl)-3-phenylpropane having the structural formula

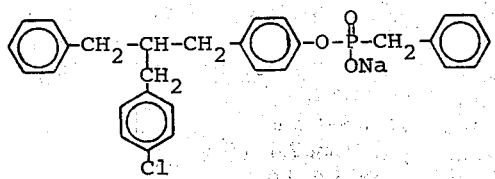

A solution of 0.195 g (0.000722 mole) of mercuric chloride in 50 ml of water was stirred for 20 minutes with 9.32 g (0.143 mole) of mossy zinc. The aqueous layer was discarded and the zinc amalgam washed with 2 × 200 ml water. After excess water was decanted 97 ml of 37% hydrochloric acid along with 97 ml of water was quickly added. Finally, a solution of 5 g (0.0143 mole) of 1-(4-hydroxyphenyl)-2-(4-chlorobenzyl)-3-phenyl-1-propanone in 50 ml of ethanol was added and the vigorously stirred mixture heated to reflux for 16 hours. The reaction mixture was allowed to cool, extracted with 2 × 200 ml of chloroform. After drying over anhydrous sodium sulfate chloroform solution was concentrated to an oil. This was chromatographed on a 600 × 24 mm silica gel column. Yield 4.4 g (91.66%).

A solution of 3 g (0.0089 mole) of 1-(4-hydroxyphenyl)-2-(4-chlorobenzyl)-3-phenylpropane in 20 ml of pyridine was added to 9.31 g (0.0445 mole) of benzylphosphonic dichloride at −10°C. The solution was left overnight at room temperature and worked up as under Example IV. Yield 4.0 g (87.5%).

EXAMPLE VII

Method of making benzylphosphonate sodium salt of 1-(4-hydroxyphenyl)-2-benzyl-3-phenylpropane having the structural formula

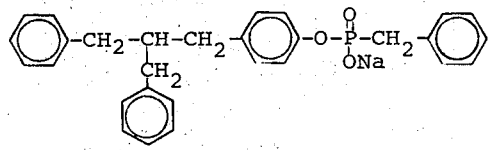

A mixture of 2.15 g Mg turning (5 × 0.024 g atom) and 2.15 g Mg powder (5 × 0.024 g atom) was added to 100 ml THF and refluxed. 5.65 g of α-chloro-4-methoxytoluene (1.5 × 0.024 moles) was added dropwise to the refluxing THF solution over 1½ hours. A solution of 5 g 1,3-diphenyl-2-propanone (0.024 moles) in 20 ml THF was added dropwise to the reaction mixture. After the completion of addition, the mixture was refluxed for 2 hours and then poured on 300 ml 20% H$_2$SO$_4$ and 200 g ice. THF layer was separated, aqueous solution was extracted with 2 × 105 ml THF, THF layer and THF extracts were combined and dried over anhydrous MgSO$_4$. THF was removed at reduced pressure; the residue was distilled at 195°–198°C/0.2 mm. Yield: 3.2 g (42.44%).

A solution of 4.3 g (0.9137 mole) of mixture obtained above in 200 ml ethyl acetate was hydrogenated at 1 atmosphere H$_2$ in the presence of 200 mg Pd/C. The absorption of hydrogen was stopped when 350 ml hydrogen was taken. Catalyst was filtered off, ethyl acetate was removed at reduced pressure to get 4.3 g colorless oil (99.3%).

To 4.3 g (0.0136 mole) of 1-(4-methoxyphenyl)-2-benzyl-3-phenylpropane was added 4 g (0.0346 mole) of pyridine hydrochloride and heated to 210°C for 5 hours. The mixture was cooled, and 300 ml H$_2$O and 300 ml chloroform were added. Chloroform layer was separated, washed with 4 × 250 ml H$_2$O and dried over anhydrous MgSO$_4$. Chloroform was removed at reduced pressure. The residue was distilled at 210°–215°C/0.3 mm. Yield 3.5 g (85.16%). This material can also be obtained by alkylation of 1-phenyl-3-(4-methoxyphenyl)-1-propanone or 1-(4-methoxyphenyl)-3-phenyl-1-propanone with α-chlorotoluene as carried out in Example I, followed by demethylation with pyridine hydrochloride and reduction of the carbonyl function.

A solution of 0.9 g (0.00297 mole) of 1-(4-hydroxyphenyl)-2-benzyl-3-phenylpropane in 10 ml of pyridine was added dropwise to 3.1 g (0.01485 mole) of benzylphosphonic dichloride in 5 ml pyridine at −10°C. The reaction mixture was kept overnight at room temperature and worked up as under Example IV. Yield 1.1 g (77.3%).

Nuclear Magnetic Resonance (Free Acid) $CDCl_3$
  δ 10.3 broad peak
  δ 7.2–7.5 multiplet
  δ 7.1 singlet
  δ 3.4 singlet
  δ 3.0 singlet
  δ 2.5 broad peak Infrared (of sodium salt) Nujol
  2920, 2885, 1620, 1520, 1495, 1470, 1450, 1360, 1320, 1260, 1235, 1190, 1175, 1150, 1120, 1080, 1065, 1035, 1020, 912, 904, 897, 841, 836, 796, 782, 751, 720 and 697 $cms^{-1}$.

EXAMPLE VIII

A. Effects on isolated smooth muscle preparations

The following compounds were tested for their effects on isolated smooth muscle preparations

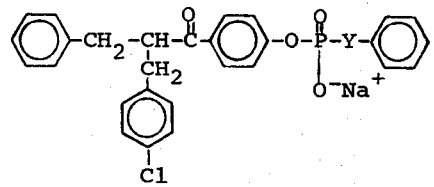

Compound 1: Y= —O—
Compound 2: Y= omitted
Compound 3: Y= —$CH_2$—

The techniques for setting up the isolated guinea pig ileum (GPI) and isolated rat fundus (RF) were those described in *Pharmacological Experiments on Isolated Preparations* (E. S. Livingston Ltd., Publishers). The tissues were bathed in Krebs solution and isotonic contractions were recorded. To elicit a maximal contraction after the initial equilibration period, the tissue (GPI or RF) was exposed to 20 ng/ml acetylcholine (ACh). After a dose-dependent pattern was established with ACh, the tissue was exposed to 20 ng/ml of $PGE_2$ in order to elicit a maximal prostaglandin-induced contraction. Test doses of $PGE_2$ and ACh which cause 50% of the maximal contractions were determined.

To test a compound for anti-prostaglandin activity, the tissue was incubated with a compound for a fixed period of time (15 minutes for the initial exposure to the test drug and 5 minutes for each successive increment in concentration) followed by the test dose of $PGE_2$ or ACh to elicit a tissue contraction. Inhibition of contraction was measured as percent reduction in the magnitude of the response to the test dose of $PGE_2$.

The concentration of drug which inhibited the test concentration of $PGE_2$ by 50% ($I.C._{50}$) was determined from the dose-response curve obtained by plotting concentration versus percent inhibition. Test contractions with ACh determined whether any decrease in contraction amplitude was specific for prostaglandin-induced contractions or a general deterioration of tissue function. The results are shown in Table 1. The term selectivitiy refers to % inhibition of ACh-induced contractions at compound dosages which inhibi the $PGE_2$-induced contraction by the indicated percentage.

Table 1

| Compound | $I.C._{50}$ (vs $PGE_2$) | | Selectivity | | |
|---|---|---|---|---|---|
| | | | 50% | 70% | 90% |
| 1 | 0.047 | μM | 0 | 0 | 0 |
| 2 | 0.20 | μM | 0 | 0 | 30 |
| 3 | 0.0061 | μM | 0 | 0 | 10–15 |

As is apparent from Table 1, compound 3 is far more potent than either of its close structural analogues. That is, compound 3 is approximately 30 times more potent than compound 2 and about 8 times more potent than compound 1.

B. Systemic Effects — Toxicities

Compounds 1–3 were tested for systemic toxicity. Male Swiss Webster mice were injected (i.p. or p.o.) with the test compound dissolved in saline (0.2 ml). The mice were examined every half hour for the first two hours after treatment and every hour for the following four hours. Thereafter the mice were examined irregularly, with a final examination at the end of the 48-hour test.

Topical toxicity was determined at a single dosage level on two hairless mice. The animals were restrained with neck collars. The test compound was applied in a total volume of 0.1 ml of 90% PEG (10% $H_2O$) spread uniformly over the back by means of a Q-tip.

The results of the toxicity studies are shown in Table 2.

Table 2

| Compound | Route | $L.D._{50}$ at 24 hours (mg/Kg) |
|---|---|---|
| 1 | i.p. | 194 |
| | p.o. | 235.2 |
| | topically | >4300 |
| 2 | i.p. | 361 |
| 3 | i.p. | 408 |
| | p.o. | 715 |
| | topically | >4350 |

As is apparent from Table 2, compounds 2 and 3 are considerably less toxic than compound 1.

We claim:
1. Phenyl- and benzylphosphonate esters having the structural formula

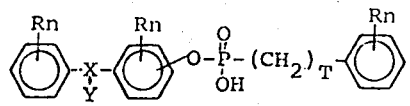

wherein X is an alkyl or alkenyl chain having 2–8 carbon atoms, one of which carbon atoms may be in the form of a carbonyl group, Y is selected from the group consisting of H, an alkyl group having 1–12 carbon atoms, phenyl, benzyl and phenyl or benzyl substituted with one or more R; and R is selected from the group consisting of H, loweralkyl, lower alkoxy, halogen, $CF_3$, $NO_2$, OH, CN, $COOR_1$, $CONR_1R_2$, $NHCOR_1$, $NR_1R_2$, and $CH_2NR_1R_2$ $R_1$ and $R_2$ are each selected from the group consisting of H and lower alkyl, R, $R_1$ and $R_2$ being the same or different, T is 0 or 1, and n is 0–5; and pharmaceutically acceptable salts thereof.

2. Compounds of claim 1 wherein X is an alkyl group having 3 carbon atoms.

3. Compounds of claim 2 wherein Y is selected from the groupsing consisting of

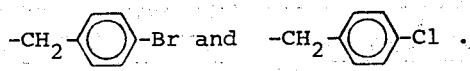

4. Compounds of claim 3 wherein the phenolic oxygen which is part of the phosphonate group is attached to the benzene ring at the 4-position.

5. Compounds of claim 4 wherein R is selected from the group consisting of H and halogen and n is 1.

6. Benzyl phosphonate esters having the structural formula

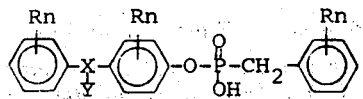

wherein X is an alkyl or alkenyl chain having 3–5 carbon atoms, one of which carbon atoms may be in the form of a carbonyl group, Y is selected from the group consisting of H,

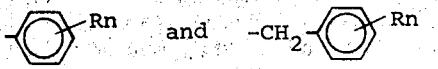

R is selected from the group consisting of H, lower alkyl, lower alkoxy and halogen; n is 0–3 and pharmaceutically acceptable salts thereof.

7. Benzylphosphonates having the structural formula

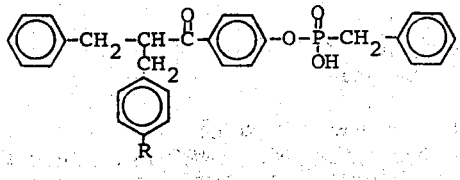

where R is selected from the group consisting of an H or halogen; and pharmaceutically acceptable salts thereof.

* * * * *